United States Patent [19]
Gobbato

[11] Patent Number: 5,961,937
[45] Date of Patent: Oct. 5, 1999

[54] UNIVERSAL DEVICE FOR THE THOROUGH CLEANING, DISINFECTING AND STERILIZING OF DENTAL, SURGICAL, AND VETERINARY INSTRUMENTS AS WELL AS FOR OTHER USES

[75] Inventor: Luciano Gobbato, Porza, Switzerland

[73] Assignee: Bitiess Microtecnica S.A., Barbengo, Switzerland

[21] Appl. No.: 08/913,157

[22] PCT Filed: Feb. 29, 1996

[86] PCT No.: PCT/IB96/00151

§ 371 Date: Nov. 26, 1997

§ 102(e) Date: Nov. 26, 1997

[87] PCT Pub. No.: WO96/41686

PCT Pub. Date: Dec. 27, 1996

[30]     Foreign Application Priority Data

Jun. 13, 1995  [CH]  Switzerland ............................. 1753/95

[51] Int. Cl.⁶ ....................................................... A61L 2/18

[52] U.S. Cl. ......................... 422/300; 422/292; 422/297; 134/104.2; 134/170

[58] Field of Search ................................ 422/28, 33, 292, 422/295, 297, 300; 134/43, 58 R, 104.2, 170

[56]     References Cited

U.S. PATENT DOCUMENTS

| | | | |
|---|---|---|---|
| 4,552,163 | 11/1985 | Biancalana et al. | 134/100 |
| 4,914,584 | 4/1990 | Gibson | 364/200 |
| 5,265,628 | 11/1993 | Sage et al. | 134/58 R |

FOREIGN PATENT DOCUMENTS

| | | |
|---|---|---|
| 0 056 791 | 7/1982 | European Pat. Off. . |
| 32 39 549 | 4/1984 | Germany . |
| 93 10 601 | 10/1993 | Germany . |
| 1 597 867 | 9/1981 | United Kingdom . |

*Primary Examiner*—Robert Warden
*Assistant Examiner*—Fariborz Moazzam
*Attorney, Agent, or Firm*—Young & Thompson

[57]     ABSTRACT

A device for the sterilization of a dental, medical or similar instrument comprising a chamber (4), preferably frusto-conical in shape or downward tapering, with two walls (1, 2) separated by a hollow space, subdivided along axis into smaller spaces (3', 3", 3'", 3""), connected to the interior of the chamber by rings of holes (5', 5", 5'", 5"") with downward pointing jets, and passing at a distance (e) from the axis (K) of the chamber (4). These jets sterilize the entire internal and external surface area of the instrument along it length. The pressure upstream of the holes (5', 5", 5'", 5""), their diameter and direction, ensures that the lower and more contaminated part of the instrument is more thoroughly treated.

9 Claims, 9 Drawing Sheets

UNIVERSAL DEVICE FOR THE THOROUGH CLEANING, DISINFECTING AND STERILIZING OF DENTAL, SURGICAL, AND VETERINARY INSTRUMENTS AS WELL AS FOR OTHER USES

FIELD OF THE INVENTION

This invention concerns a universal device for the thorough—i.e. external and internal—cleaning and disinfecting of dental, surgical and veterinary instruments and for other uses such as dental instruments, scalpels, probes, endoscopes, mirrors, forceps, etc. both in their assembled form and stripped down to their individual components. This device completely removes viral contamination which can be easily transmitted.

BACKGROUND OF THE INVENTION

Similar equipment already exists, e.g. that described in European patent No. 56 791 or U.S. Pat. No. 4,552,163, being the property of the applicant. With these devices, the instrument to be disinfected is placed vertically into a cylindrical chamber and jets of water and/or disinfectant mixed with air, are directed towards the vertical axis of the chamber and strike specific points of the front of the instrument. After striking the instrument, the jets rebound towards the walls of the chamber where gravity causes them to fall downwards. Consequently, there are a number of areas which are not sprayed or only partially sprayed by said liquids, thereby leaving an unwanted bacterial residue. This is particularly true in the lower part of the chamber where, in the case of dental instruments for example, there are usually areas which are more contaminated by germs. This is an unwanted and worrying problem.

SUMMARY OF THE INVENTION

The inventor of this device has overcome this problem by modifying the shape of the chamber and varying the direction and intensity of the jets ensuring that the disinfectant is sprayed over the entire surface area of the instrument being treated, with greater and more effective action being exerted on the lower parts of the instrument which, as has been said, are the most contaminated areas.

More specifically, this invention is a universal device designated to clean and sterilize both internally and externally, dental, surgical, veterinary and other types of instruments. It consists of a chamber with an internal and an external wall, separated by a hollow space, with holes on the internal wall through which fluids/liquids and/or air are sprayed in a pre-set sequence on to the instrument placed vertically in the chamber. The hollow space between the two walls is subdivided along the axis of the chamber into several smaller chambers along which is a ring of spray holes inclined at a specific downward angle moving off-centre at a predetermined distance from the vertical axis of the chamber. The shape of the chamber and the pressure upstream of the holes and/or their diameter and direction causes the jets to move in a helicoidal manner, with the speed and kinetic energy increasing from the upper to the lower part of the chamber.

According to one of the embodiments, said chamber has a downward tapering frusto-conical shape.

Two variations of the device have been constructed: one which does not require the dismantling of the instruments to be treated, the other requiring it to be stripped down to its various component parts with each component being treated separately.

The importance of this newly invented device is its ability to thoroughly clean, disinfect and sterilize an item of dental equipment for example, whilst the patient is being treated, i.e. whilst the work is being carried out, because the instrument is washed, disinfected, sterilized and lubricated externally and internally without having to remove it or disconnect it from the electric or pneumatic cable and from the water cooling pipe. Inside the cylinder, the instrument is activated at the time of the disinfecting and sterilizing process to remove the pathogens from the internal ducts of same and when it is switched off, the disinfecting and sterilizing liquid is aspirated in the same manner as the contaminated part. In this way, when the disinfecting and sterilizating substance enters the chamber of the device, the same sterilization process is repeated at least two or three times in the patient's mouth i.e.: when the instrument is switched on and off. The various operations are activated by means of electrical impulses controlled by electronic cards.

BRIEF DESCRIPTION OF THE DRAWINGS

The attached drawings are some of the embodiments of the device in question which are not exhaustive or binding.

DESCRIPTION OF THE PREFERRED EMBODIMENTS

Figure 1A:
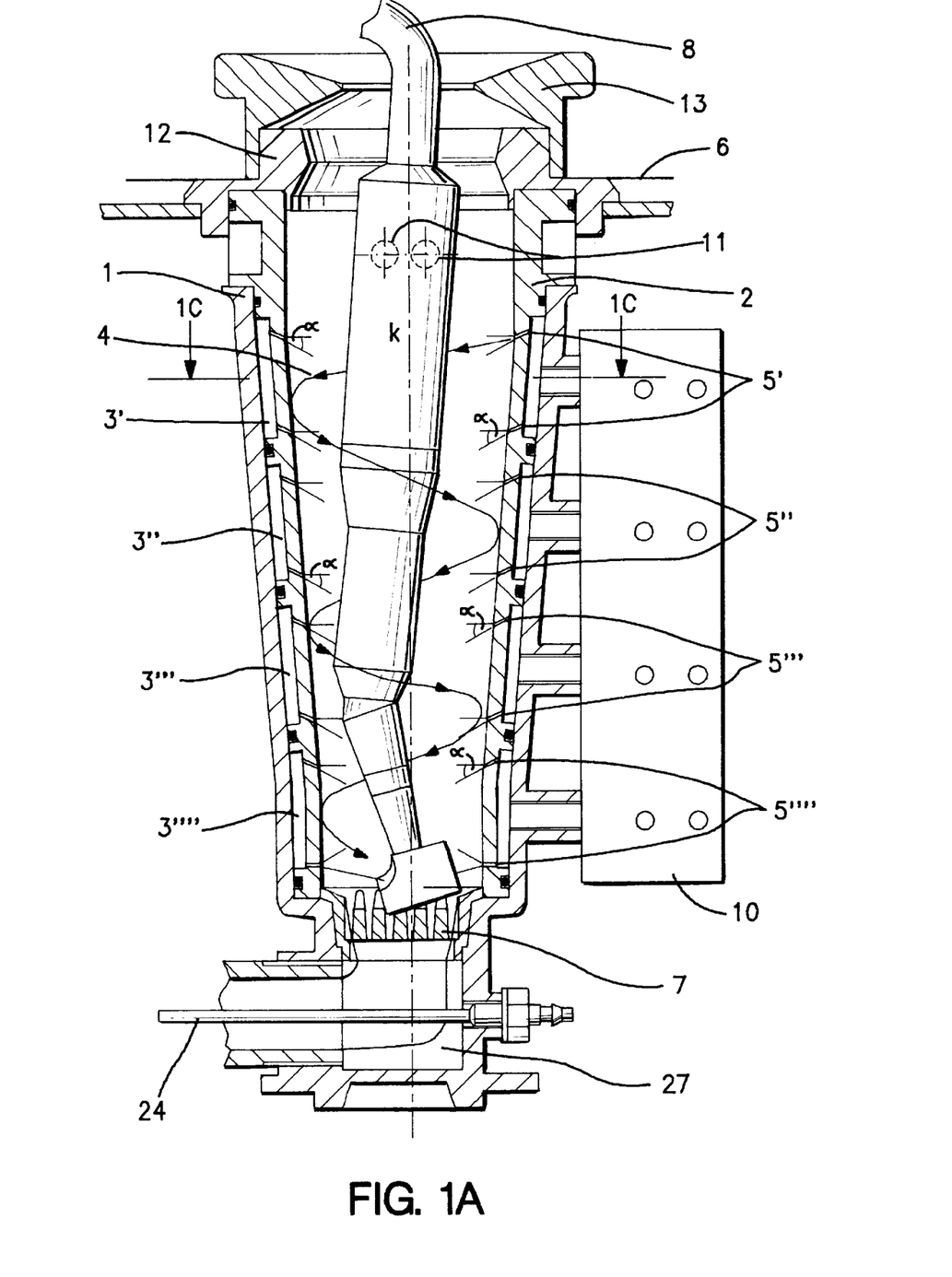
FIGS. 1a and 1b are two embodiments of the invention where a dental instrument is cleaned, disinfected and sterilized externally and internally without stripping it down to its component parts.

The device shown in figure 1a includes the chamber 4, preferably of a frusto-conical shape or, in any case, tapering downwards, with its external 1, and internal 2 walls, separated by a hollow space, subdivided along the axis into smaller conical toroidal spaces 3', 3", 3'", 3"". The internal wall 2 has a number of holes 5', 5", 5'", 5"", etc. positioned offcentre so that the jets originating from the holes pass at a pre-fixed distance e, from the vertical axis K of the chamber. They are also directed downwards creating powerful helicoidal jets of air, water and disinfectant directed on to the instrument 8 to be cleaned, dried and/or lubricated. Thus, the jets cover simultaneously the entire surface of the instrument to be treated.

This newly invented device differs from the other conventional types in that it not only disinfects, dries and lubricates, but also sterilizes the instrument in the chamber externally and internally without having to strip it down to its component parts and removing it from its support, which is a major advantage in the case of dental equipment for example.

At the base of the chamber 4, there is a normal mesh type filter 7, which can be easily removed and washed or replaced, and a standard type chamber 27, operating on the Venturi principle, comprising a pipe 24, fitted with a nozzle, not shown, which blasts a jet of air to remove the contaminated water following the use of an instrument.

Figure 2:
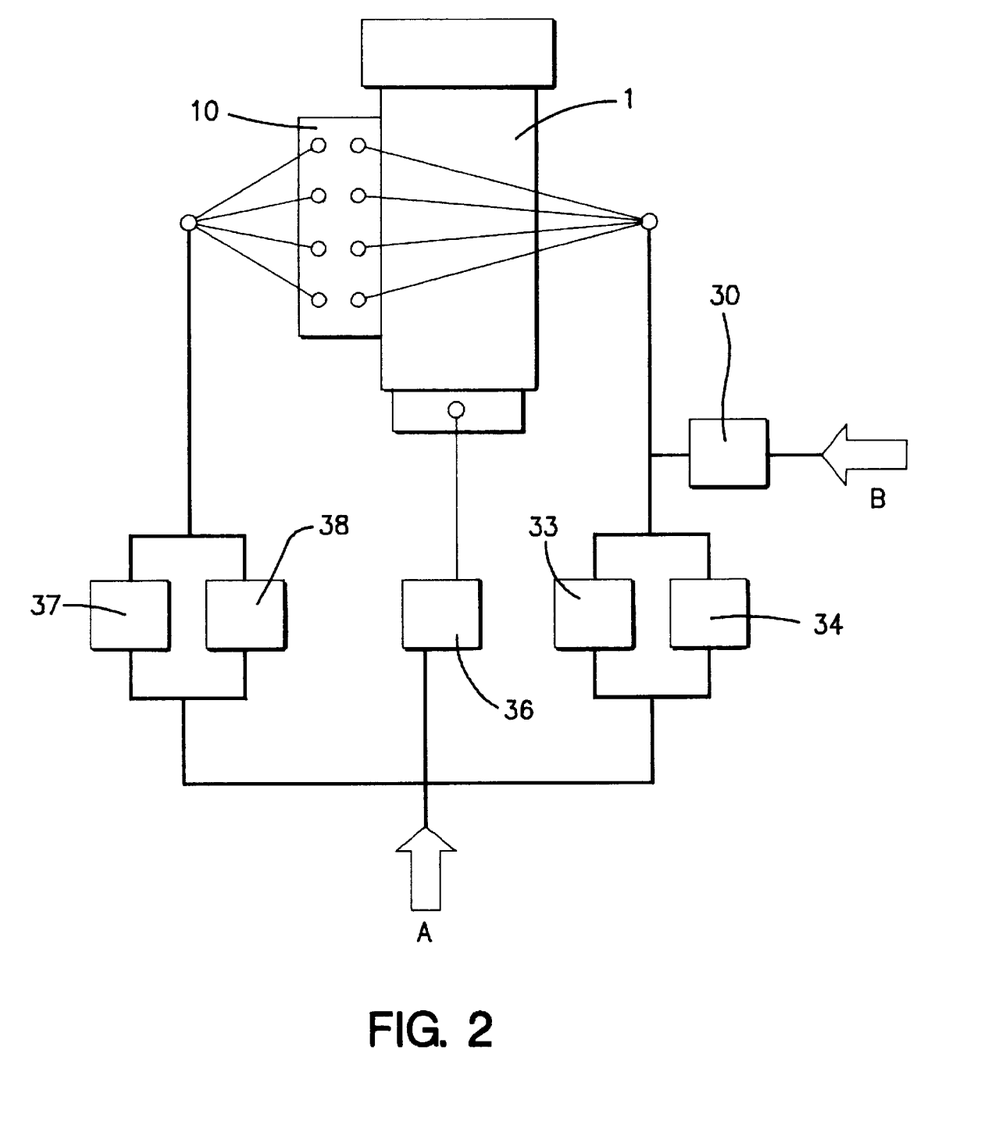
FIG. 2 is a diagram of the valves opening and closing cycle activating the internal and external cleaning, disinfecting, sterilizing and drying of the instrument placed inside the device.
Figure 3:
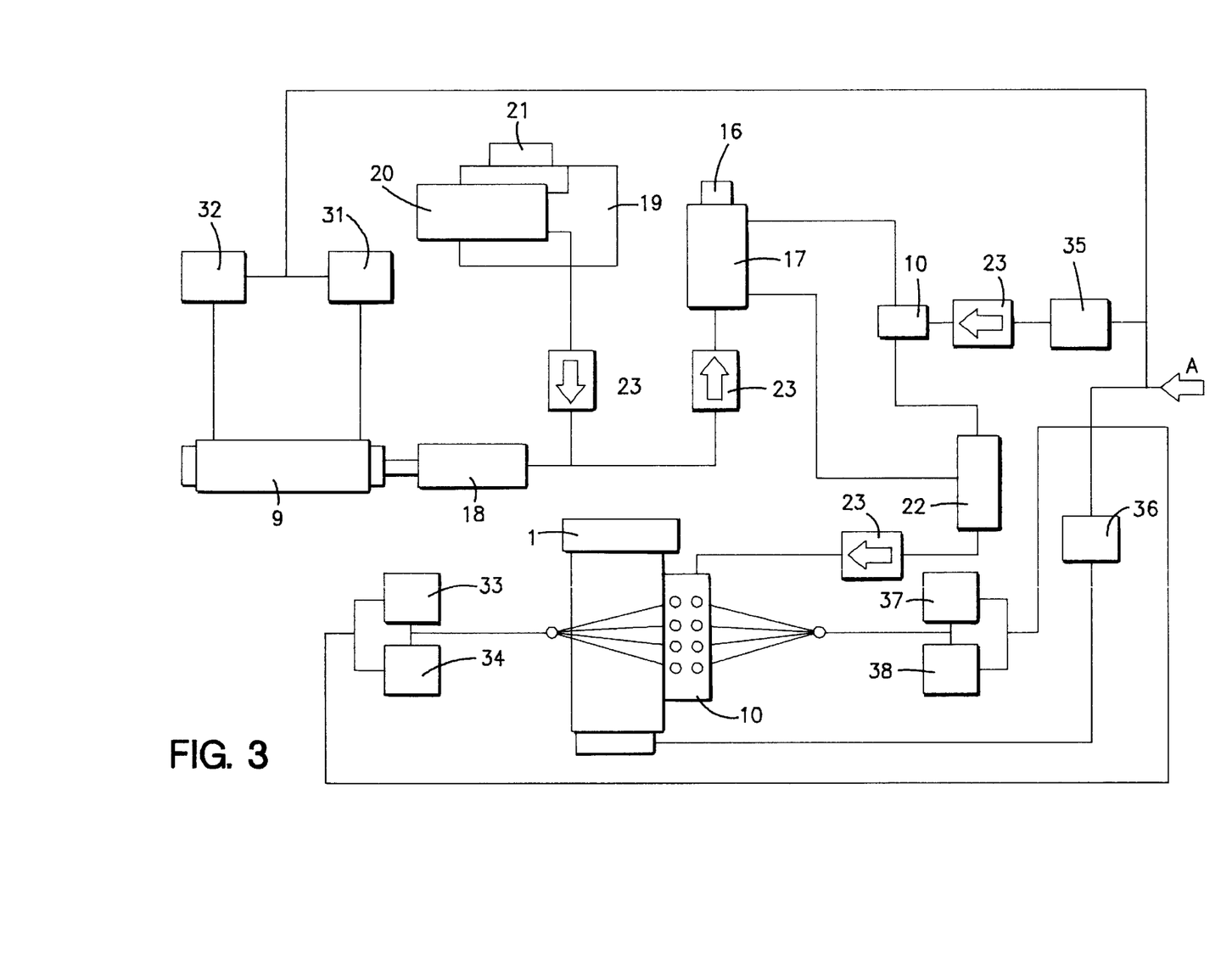
FIG. 3 is a diagram of the electro valves used in disinfecting and sterilizing the instruments placed in the device according to FIGS. 1a, 1b, and 2.

Pipes lead from the manifold 10, to valves 30, 31, 32, 33, 34, 35, 37, 38 shown in detail in FIGS. 2 & 3, which control the various stages of the cleaning and disinfecting cycle.

These valves are a new invention and will be explained in detail later on.

With reference to FIGS. 1a, 1b, 1c, 2, 3, an explanation will now be given of the disinfection and sterilization procedure of a dental instrument according to the invention without the need to strip it down to its component parts and removing it from its support.

The dirty instrument 8 (FIGS. 1a and 1b) is placed in the chamber without disconnecting it from the electric or pneumatic cable and the water cooling pipe, the reasons for which are twofold:
a) to allow the operation to be carried out rapidly and expeditiously, preventing wear of the connections;
b) to activate the instrument inside the chamber at the moment of disinfection and sterilization to eliminate the pathogens present in the internal ducts of the instrument and, when the machine is switched off, to remove by suction the disinfecting and sterilizing fluid from the areas potentially contaminated. In this way, all the internal and external contaminated parts of the instrument are thoroughly cleaned, disinfected and sterilized.

When the instrument is inserted into the chamber 4, to avoid contamination of the opening 12 (FIGS. 1 and 1b) of same, a pierceable membrane 6 is out in place (FIGS. 1a, 1b and 7) preferably made of cellulose, impregnated with disinfecting and sterilizing fluid, used respectively during the disinfection and sterilization stages. This membrane is fixed in position at the opening 12 by means of a ring nut and is pierced when the instrument 8 is placed inside.

Figure 7:
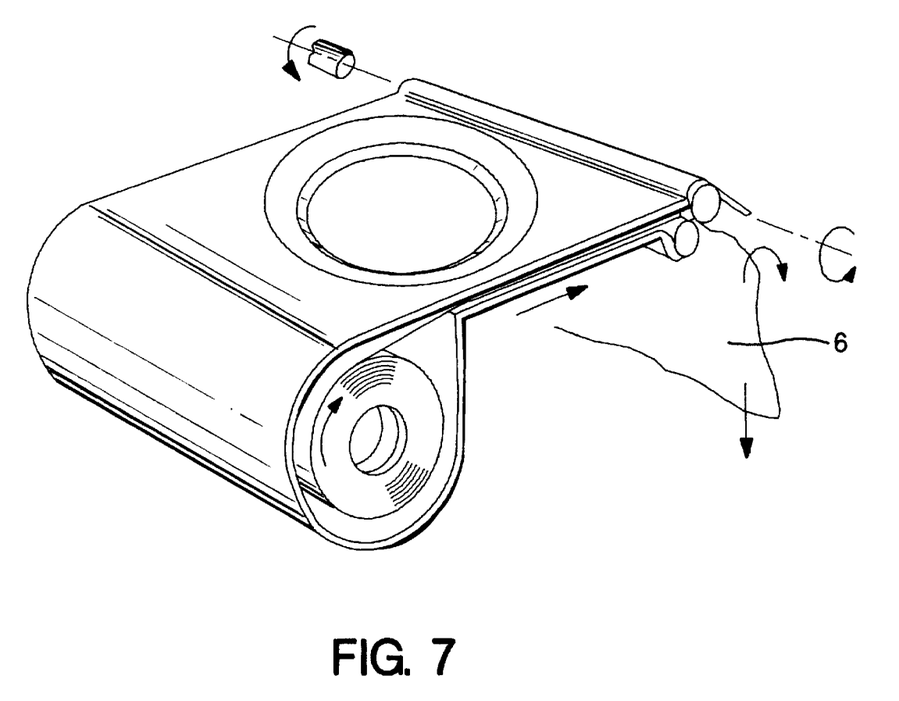
FIG. 7 shows a membrane dispensing device.
Figure 8:
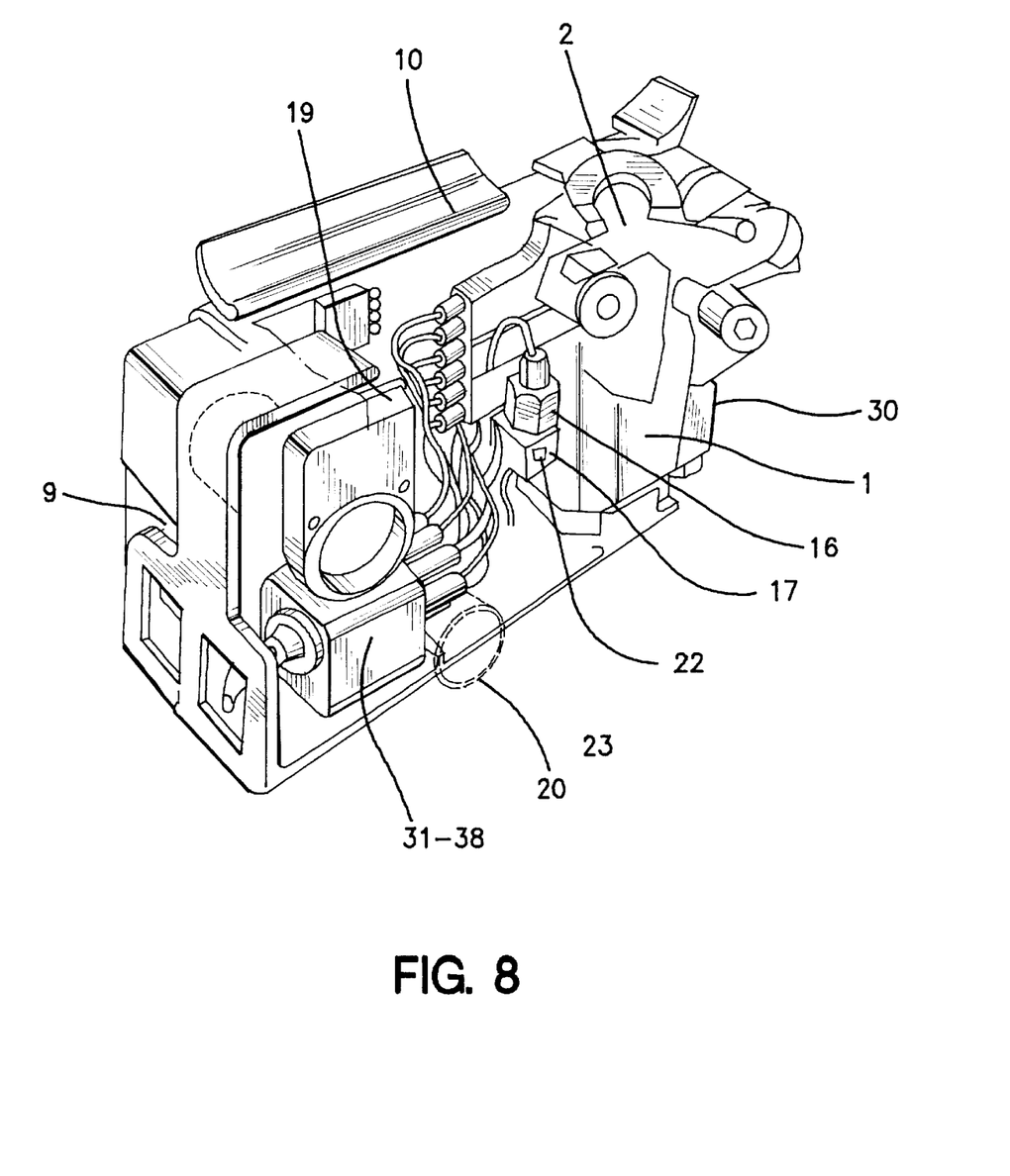
FIG. 8 is an example of the arrangement of the various components of the device in question, based on another embodiment.

The pierced membrane 6, is removed on completion of the sterilization cycle before removing the instrument, or else is wound on by means of a miniature motor and is then re-wound into a special container which is removed when full. Such a special container for dispensing cellulose membrane is depicted in FIG. 7.

The disinfection and sterilization unit (FIG. 3) consists of the following parts:
31, 32, 33, 34, 35=electro valves
9=double-acting pneumatic cylinder or membrane pump;
16=sensor controlling the presence of the disinfecting or sterilizing fluid;
17=chamber for loading and discharging the single dose of disinfecting or sterilizing liquid, aspirated by 9 and controlled by 16;
18=aspiration and dosing chamber of the disinfecting and sterilizing fluid contained in the cartridge 20;
19=support for holding and perforating the cartridge;
20=cartridge containing the disinfecting or sterilizing liquid which must be replaced after a specified number of operations;
21=micro switch sensing the presence of the cartridge;
22=nebulizer;
10=manifold;
A=compressed air inlet;
23=one-way valves.

The operating principle is as follows:
The pneumatic cylinder or pump 9 (FIG. 3), not shown in FIGS. 1a and 1b aspirates a single dose of disinfecting or sterilizing fluid from the cartridge 20 through the chamber 18, and then sends it on to the loading chamber 17, controlled by the sensor 16.

The sensor 16 senses the presence of the disinfecting or sterilizing fluid and allows the cycle to proceed.

At the pre-arranged moment, the valve 35 opens, and the single dose is sent to the nebulizer 22 whence it passes into the manifold 10 which sends it on to the cylinder 1 with the help of the valves 33, 34.

Figure 1B:
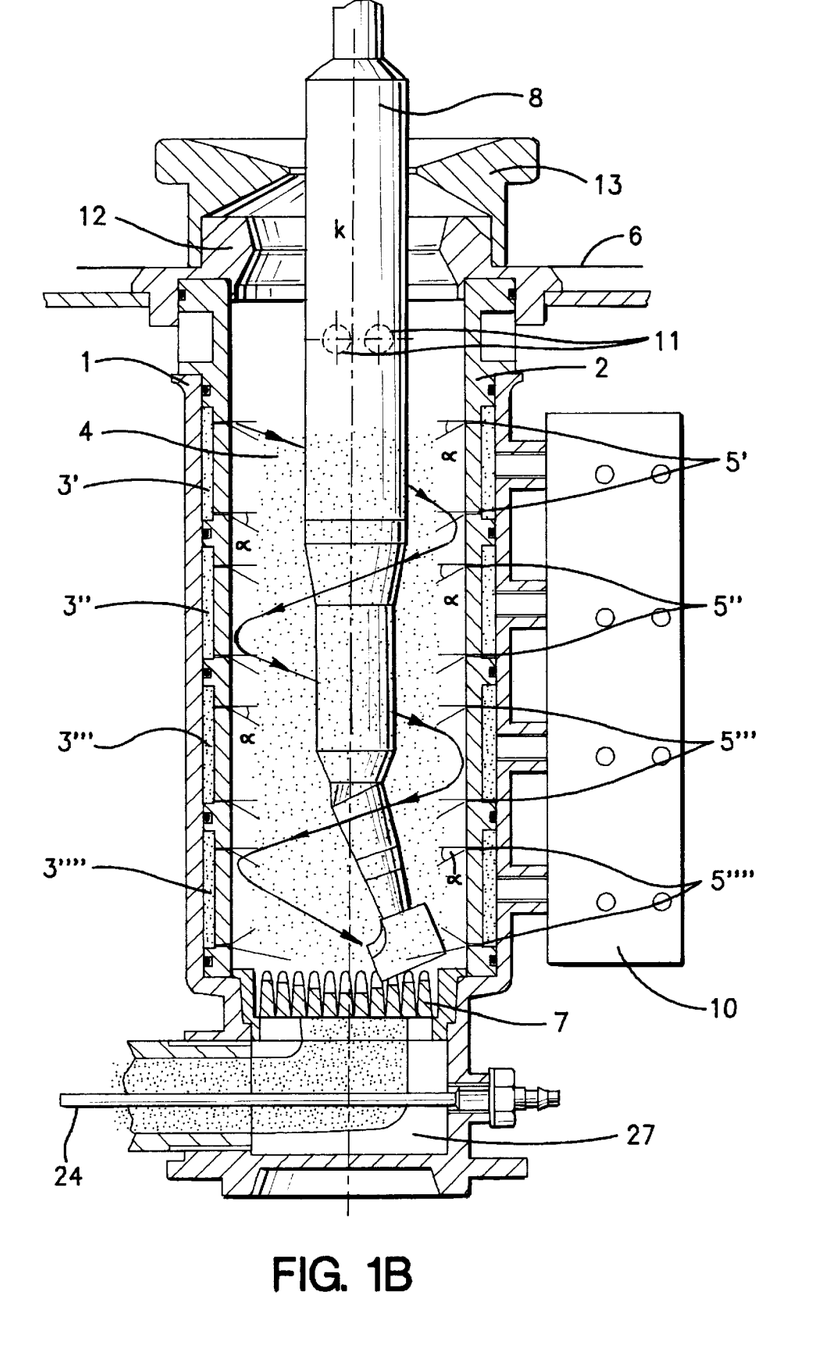

Below is a description of the washing/drying and disinfecting and sterilizing cycle of the device as shown in FIGS. 1a and 1b.

During the initial washing and drying stage of the instruments, the valves 33, 34, 36, 37, 38 and 30 open and a mixture of air A and water B is sent through the manifold 10 and washes the instrument 8.

The air is sent through valve 36 to the discharge point to create an aspiration effect in the chamber 1.

Valve 30 (FIG. 2) then closes and valves 33, 34 & 36 remain open, sending the air to the manifold 10 to dry the instrument and, simultaneously, to the discharge point, to continue the aspiration effect.

The full washing-drying-disinfecting and sterilizing cycle which takes place in the chamber 1, 2 is the innovative and unique aspect of this device.

Its conical or tapered shape (wide at the mouth and narrow at the base) means that inside the chamber during the washing and sterilizing stages and by means of four rings of 48 holes in all, with the passing off centre at a distance e, from the axis K of the chamber and inclined downwards at an angle α (FIG. 1c), a swirling effect is produced around the instrument 8, in a downward direction towards the head of the instrument causing solid and non-solid particles on the head to be detached and drawn towards the discharge point.

Figure 1C:
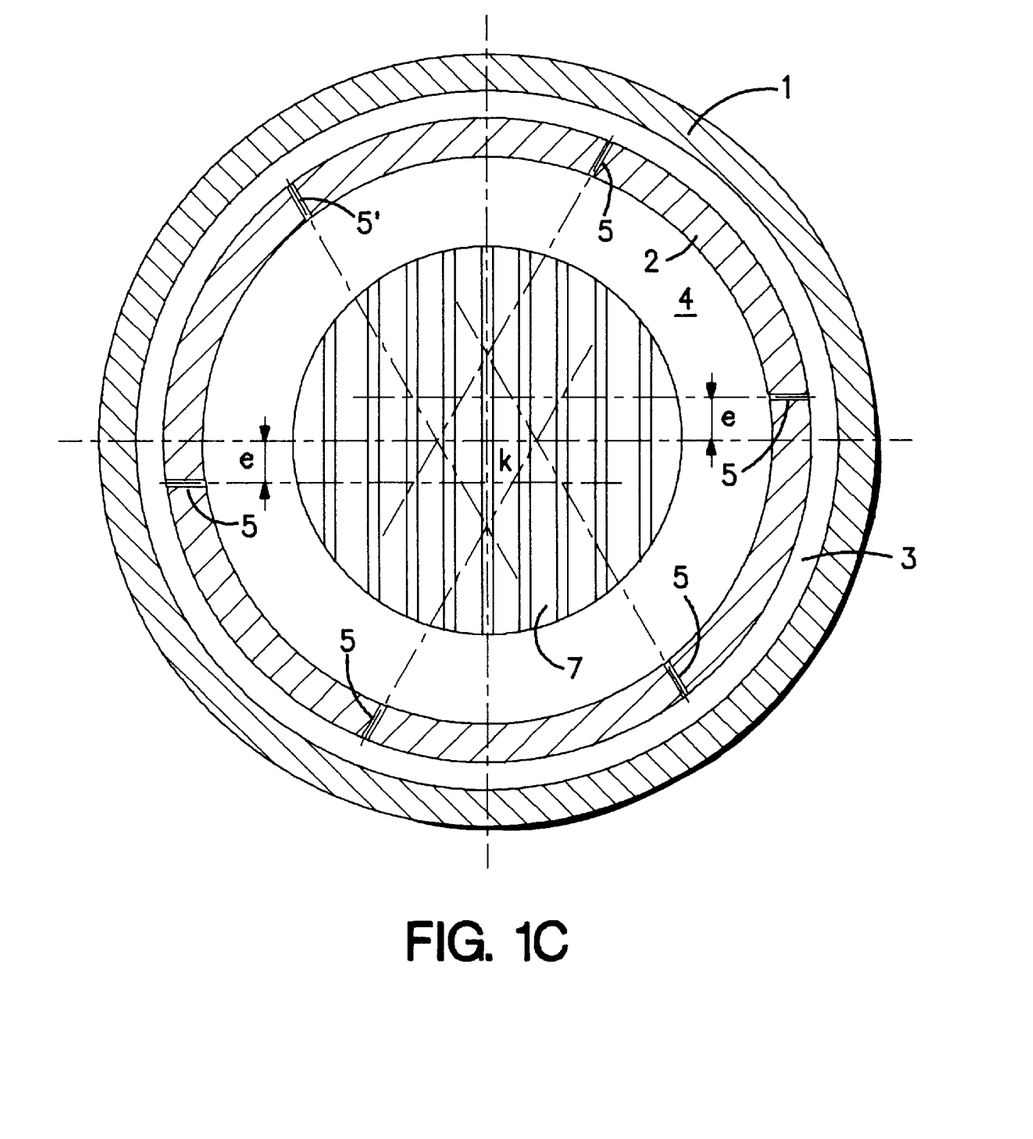
FIG. 1c is a cross-section of the above, showing the direction of the jets.

The dimensions of the holes are such that the fluid flowing from them strikes the instrument to be treated with a kinetic force which increases as it flows downwards from the top to the lower part of the chamber where the head, i.e. the most contaminated part, is located.

In addition, during the disinfecting cycle, particular attention has been given to the problem of pathogens inside a dental instrument caused, as already mentioned, by the aspirating action of the instrument inside the patient's mouth whilst deactivated, to prevent a loss of the cooling water.

Consequently, the device has been designed so that when the disinfecting or sterilizing fluid is introduced into the hollow spaces 3', 3", 3'", 3"" and 5', 5", 5'", 5"" (FIGS. 1a and 1b), it repeats twice (or even three times, by means of a program switch on the electronic card) the same process of disinfecting and sterilization as in the patient's mouth (the switching on and off of the instrument). This dual (or triple) action requires the instrument to remain connected to the electric or pneumatic cable and to the water pipe to enable it to receive the above-mentioned two (or three) impulses. This causes the instrument to discharge the contaminated substances still inside it and subsequently take in the disinfecting or sterilizing fluid.

The residual disinfecting or sterilizing fluid is then rinsed from the instrument which is then dried.

Figure 4:
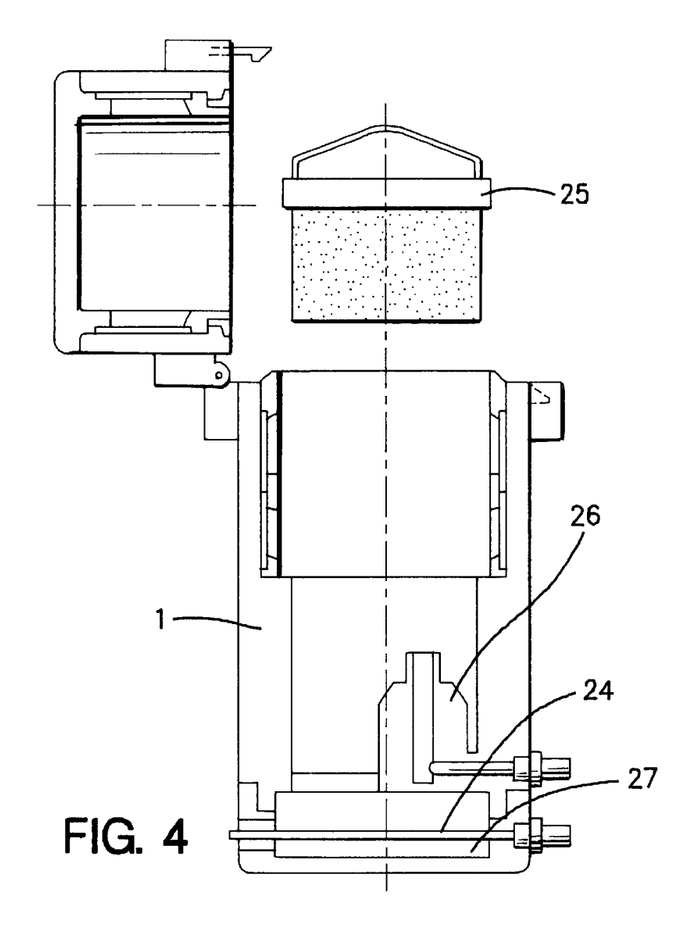
FIGS. 4 and 5 represent embodiments of the device according to the invention using a permeable container for holding small instruments.
Figure 5:
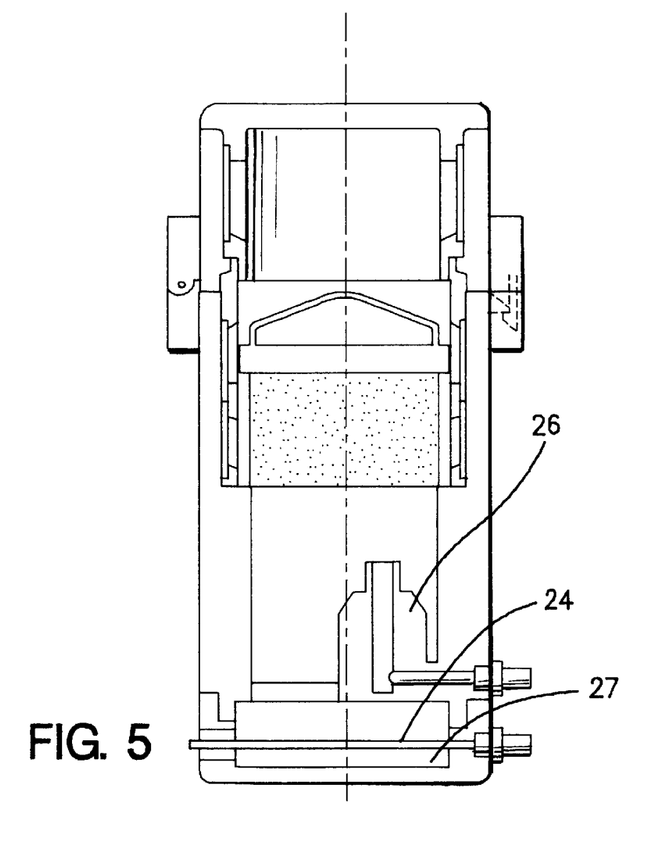

The device may comprise a support 26 (FIGS. 4 and 5) for housing a head of the instrument for internal and external treatment with jets of water, disinfecting and sterilizing fluid, air, lubricant for cleaning, disinfecting, sterilizing, drying and lubricating.

The device may also include a permeable container 25 (FIGS. 4 and 5) for holding small instruments such as burrs to be cleaned.

Figure 6A:
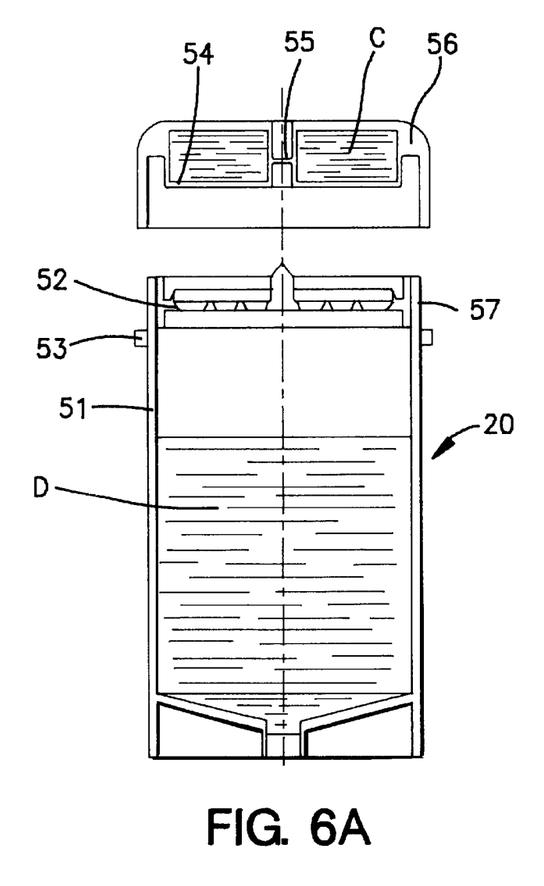
FIGS. 6a, 6b and 6c represent another embodiment of the device according to the invention, for mixing distilled water and disinfectant just prior to use.
Figure 6B:
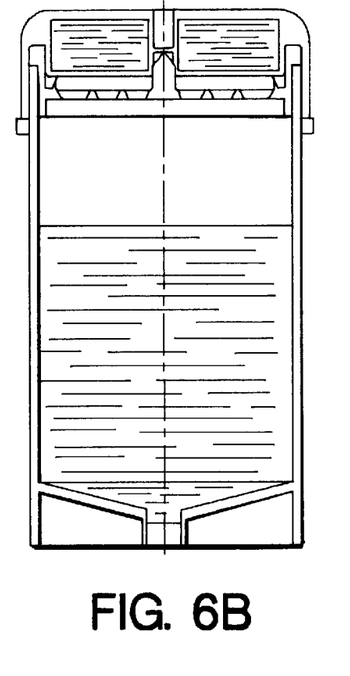
Figure 6C:
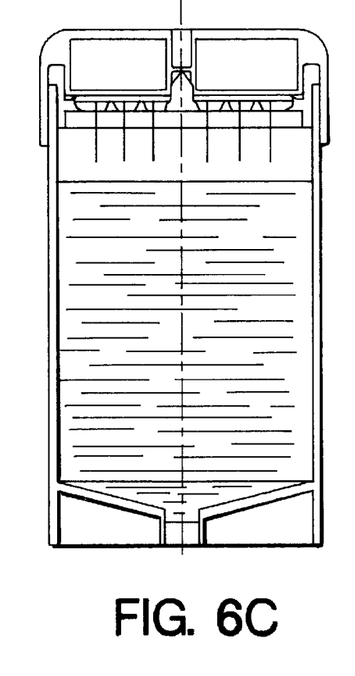

The cartridge 20 containing the disinfecting or sterilizing solution is preferably comprised of two separate chambers C and D (FIGS. 6a and 6b). Chamber C contains the disinfectant, whereas chamber D contains distilled water. Just prior to use, the two fluids are mixed by removing a seal 53 and twisting a cap 56 on the cartridge unit 57. This action pierces a first diaphragm 52 at a specific point and then a second diaphragm 55 which allows air to enter.

I claim:

1. A device for the thorough external and internal cleaning and sterilizing of dental, surgical and veterinary instruments, comprising a chamber having a downward tapering, frusto-conical shape with an external wall, an internal wall, separated by a hollow space with holes on the internal wall through which fluids, liquids, and/or air are sprayed in a pre-set sequence on to the instrument to be sterilized, arranged vertically inside the chamber, the hollow space being subdivided along a vertical axis of the chamber into smaller chambers, each of said smaller chambers having a number of said holes with jets, said holes being inclined at a downward angle passing off-center at a specific distance from the vertical axis of the chamber; the shape of the chamber and the pressure upstream of the holes and/or their diameter, as well as their direction, being selected so as to cause the jets to rotate in a swirling movement with increasing speed and kinetic energy downwards from the top of the chamber; and a pierceable membrane disposed at a mouth of the chamber in order to prevent contamination of the instrument.

2. The device according to claim 1, further comprising an aspiration and expulsion mechanism, whereby during a sterilization cycle, said mechanism carries out a series of aspirations and expulsions from the instrument in order to expel contaminated residues from a lower end of the instrument and introduce into the instrument the disinfectant located in an ante-chamber.

3. The device according to claim 1, further comprising nine electro-valve means for introducing into the hollow space, firstly a mixture of air and water to wash the instrument in the chamber, and secondly, air for drying; and another valve for activating an aspirating effect in the chamber, which is followed by disinfecting and sterilizing phases.

4. The device according to claim 1, further comprising a dual-acting pneumatic pump means for aspirating a single dose of disinfectant from a disinfectant cartridge, and transferring said dose from a dosing chamber to a control chamber; a sensor for signaling the presence of disinfectant and allowing a disinfecting cycle to proceed, a valve being then opened allowing the disinfectant to be sent on to a nebulizer through which the disinfectant passes in a manifold for distribution to the chamber with the aid of valve means.

5. The device according to claim 1, further comprising a support for housing a head of the instrument for internal and external treatment with jets of water, disinfecting and sterilizing fluid, air, lubricant for cleaning, disinfecting, sterilizing, drying and lubricating.

6. The device according to claim 1, further comprising a permeable container for holding small instruments and burrs for cleaning; and a drainage hole located at the base of the chamber.

7. The device according to claim 1, further comprising first valve means for aspirating disinfectant, second valve means for injecting the disinfectant into a control chamber, a plurality of valves for washing, a plurality of valves for drying, and a plurality of valves for disinfecting.

8. The device according to claim 1, further comprising a cartridge containing a disinfecting fluid, said cartridge having a cartridge unit and two separate chambers, a first chamber containing a disinfectant and a second chamber containing distilled water; whereby just prior to use, the disinfectant and the distilled water are mixed by removing a seal and twisting a cap on the cartridge unit to pierce a first diaphragm at a specific point and then a second diaphragm which allows air to enter.

9. The device according to claim 1, wherein the pierceable membrane is impregnated with disinfecting and sterilizing fluid, and secured by a ring nut at the mouth of the chamber, said membrane being pierced when the instrument is inserted and then removed on completion of a sterilization cycle.

* * * * *